United States Patent [19]

Warner

[11] Patent Number: 4,992,047
[45] Date of Patent: Feb. 12, 1991

[54] SURGICAL SUCTION TOOL

[76] Inventor: Charlene Warner, Rte. 7 Box 7890, Nacogdoches, Tex. 75961

[21] Appl. No.: 459,251

[22] Filed: Dec. 29, 1989

[51] Int. Cl.[5] .................. A61C 17/06; A61C 1/00; A61N 1/30
[52] U.S. Cl. ........................... 433/91; 433/29; 433/94; 433/95; 604/20
[58] Field of Search .............. 433/29, 91, 93, 94, 433/95; 604/20, 21; 128/634

[56] References Cited

U.S. PATENT DOCUMENTS

| | | | |
|---|---|---|---|
| 2,531,730 | 11/1950 | Henderson | 433/91 |
| 2,711,586 | 6/1955 | Groves | 433/95 |
| 4,281,986 | 8/1981 | Erickson | 433/93 |
| 4,477,252 | 10/1984 | Lieb et al. | 433/29 |
| 4,872,837 | 10/1989 | Issalene et al. | 433/29 |

Primary Examiner—John J. Wilson
Assistant Examiner—C. Cherichetti
Attorney, Agent, or Firm—Leon Gilden

[57] ABSTRACT

A tool is set forth defined by elongate main body with a forwardly positioned leg defined by a central bore directed through the main body and forward leg, with an enlarged cylindrical knurled handle mounted rearwardly of the main body for securement thereof for positioning interiorly of an individual's mouth cavity. The tool is geometrically configured to enchance comfort and use in its application within the cavity. A modified configuration of the invention includes a fiber optic cable superimposed within an overlying chamber mounted coextensively with the main body and forward leg, wherein the main body and forward leg extend to the forward terminal end of the forward leg to enhance viewing interiorly of the mouth cavity. A further modified configuration of the instant invention includes a valve positioned to the main body and formed with a reciprocating blade to enable manual modification of vacuum directed through the tool. The invention further contemplates the use of spaced grommets mounted on the forward leg to enhance positioning of the forward leg interiorly of the mouth cavity.

4 Claims, 4 Drawing Sheets

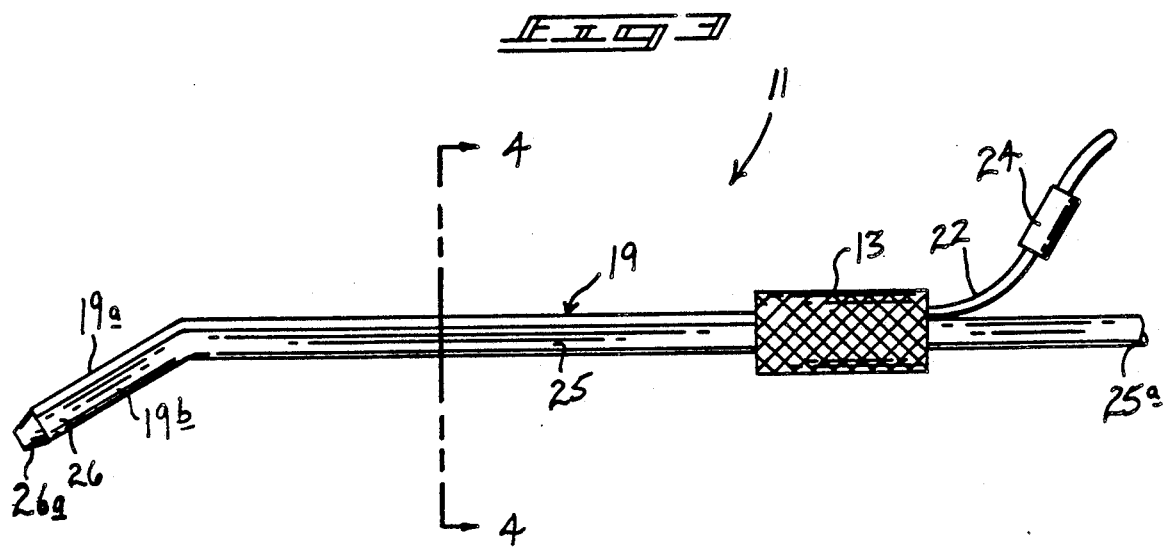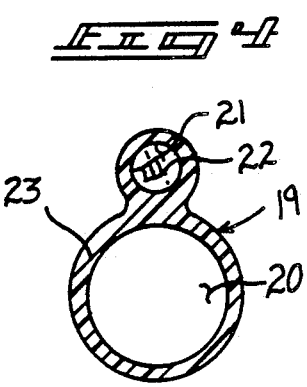

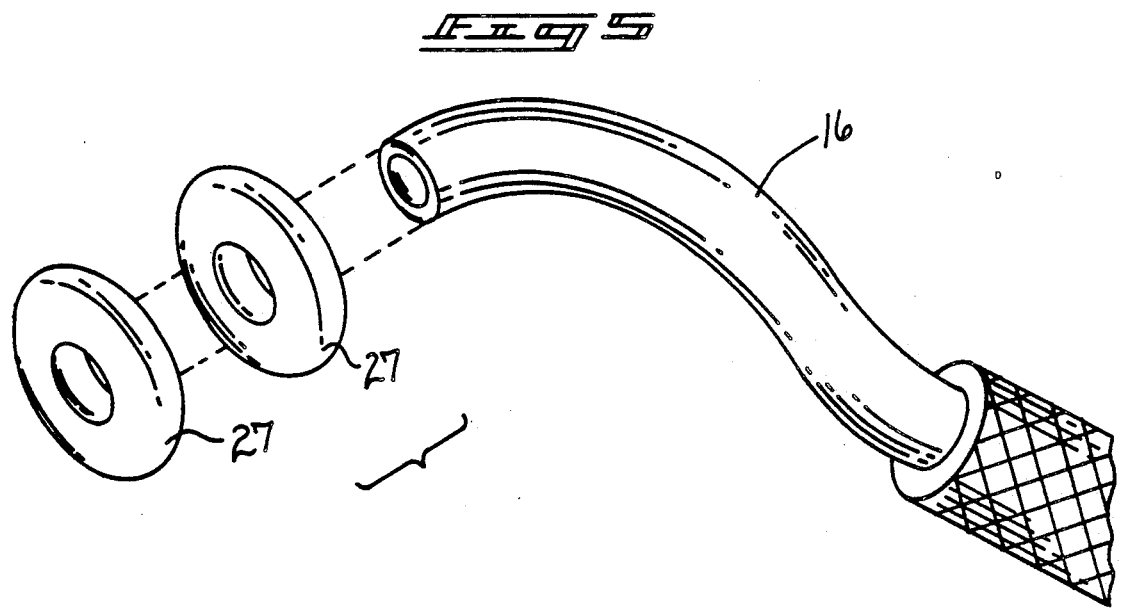
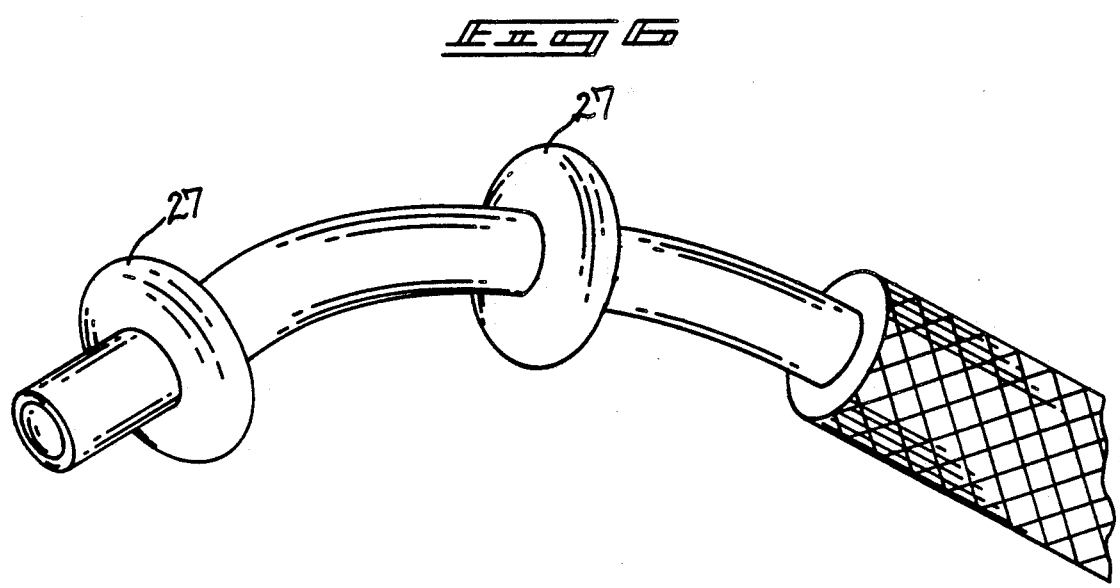

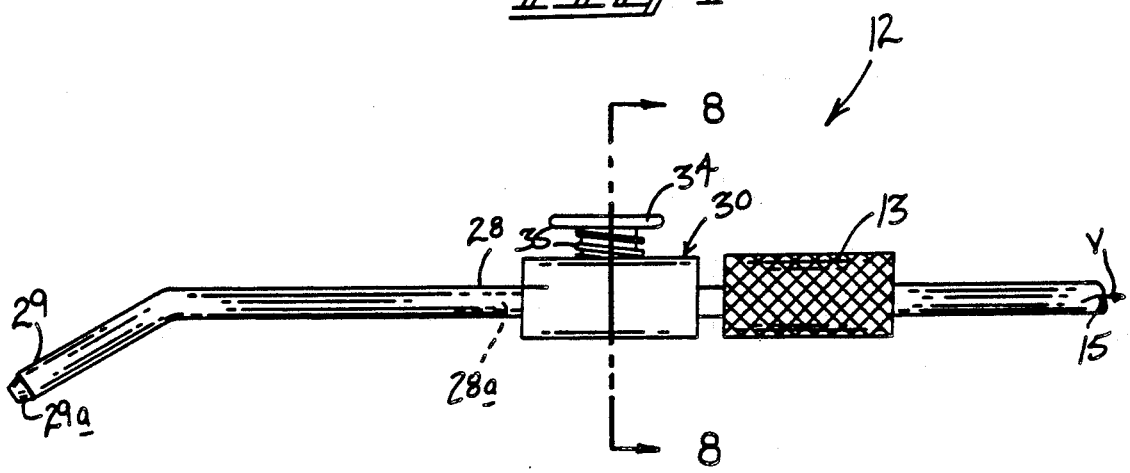
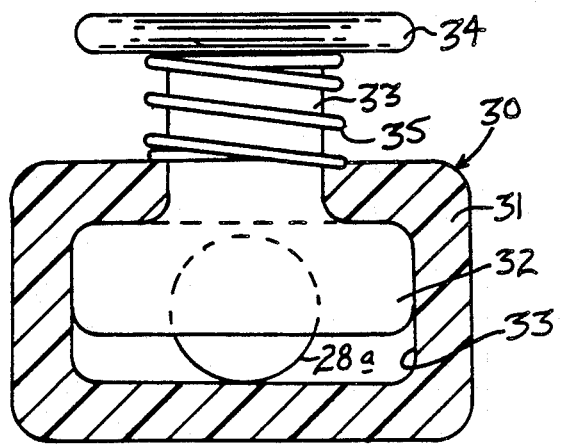

SURGICAL SUCTION TOOL

BACKGROUND OF THE INVENTION

1. Field of the Invention

The field of invention relates to surgical suction tools, and more particularly pertains to a new and improved surgical suction tool wherein the same is configured for enhanced use and positioning within an individual's mouth cavity to include means to enhance positioning within the mouth cavity, as well as optional illumination means to provide illumination within the mouth cavity.

2. Description of the Prior Art

The use of suction tools for positioning within a mouth cavity is known in the prior art for the removal of saliva, liquid, and various debris from the mouth cavity, such as in use during a dental procedure. Examples of the prior art include U.S. pat. no. 3,557,456 to Hutchinson providing a suction tool formed with a tapered lower end to provide clearance for access of dental tools within the mouth cavity.

U.S. pat. no. 2,504,557 to Lumian sets forth a suction tool formed with a "U" shaped forward leg and formed with a series of passages formed through a forward tip of the leg for direction of fluid therethrough.

U.S. pat. no. 3,885,312 to Nordin sets forth a saliva extractor wherein a plurality of tubes are configured for a partial telescoping relative to one another for enhanced positioning within a mouth cavity.

U.S. pat. no. 2,574,135 to Ward sets forth a saliva vacuum tool formed with a forward slotted tip to provide enhanced access of the saliva interiorly of the vacuum bore of the tool.

U.S. pat. no. 2,859,518 to Cohn sets forth a vacuum tool for use in a dental procedure wherein the tool includes a lower clamp to impose pressure upon an exterior surface of the jaw of an individual for enhanced securement of the tool interiorly of an individual's mouth.

As such, it may be appreciated that there is a continuing need for a new and improved surgical suction tool wherein the same addresses both the problems of unique configuration for positioning in a combination of a myriad of individuals in a dental procedure, as well as convenience in its application and in this respect, the present invention substantially fulfills this need.

SUMMARY OF THE INVENTION

In view of the foregoing disadvantages inherent in the known types of suction tools now present in the prior art, the present invention provides a surgical suction tool wherein the same is uniquely configured for its application and use in various surgical and dental procedures. As such, the general purpose of the present invention, which will be described subsequently in greater detail, is to provide a new and improved surgical suction tool which has all the advantages of the prior art suction tools and none of the disadvantages.

To attain this, the present invention includes a tool defined by an elongate main body with a forwardly positioned leg defined by a central bore directed through the main body and forward leg, with an enlarged cylindrical knurled handle mounted rearwardly of the main body for securement thereof for positioning interiorly of an individual's mouth cavity. The tool is geometrically configured to enhance comfort and use in its application within the cavity. A modified configuration of the invention includes a fiber optic cable superimposed within an overlying chamber mounted coextensively with the main body and forward leg, wherein the main body and forward leg extend to the forward terminal end of the forward leg to enhance viewing interiorly of the mouth cavity. A further modified configuration of the instant includes a valve positioned to the main body and formed with a reciprocating blade to enable manual modification of vacuum directed through the tool. The invention further contemples the use of spaced grommets mounted on the forward leg to enhance positioning of the forward leg interiorly of the mouth cavity.

My invention resides not in any one of these features per se, but rather in the particular combination of all of them herein disclosed and claimed and it is distinguished from the prior art in this particular combination of all of its structures for the functions specified.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved surgical suction tool which has all the advantages of the prior art suction tools and none of the disadvantages.

It is another object of the present invention to provide a new and improved surgical suction tool which may be easily and efficiently manufactured and marketed.

It is a further object of the present invention to provide a new and improved surgical suction tool which is of a durable and reliable construction.

An even further object of the present invention is to provide a new and improved surgical suction tool which is susceptible of a low cost of manufacture with regard to both materials and labor, and which accordingly is then susceptible of low prices of sale to the consuming public, thereby making such surgical suction tools economically available to the buying public.

Still yet another object of the present invention is to provide a new and improved surgical suction tool which provides in the apparatuses and methods of the prior art some of the advantages thereof, while simultaneously overcoming some of the disadvantages normally associated therewith.

Still another object of the present invention is to provide a new and improved surgical suction tool wherein the same provides a unique configuration for grasping of the tool and positioning of the tool interiorly of an individual during a dental or surgical procedure.

These together with other objects of the invention, along with the various features of novelty which characterize the invention, are pointed out with particularly in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 3 is an orthographic side view of a modified tool utilized by the instant invention.

FIG. 4 is an orthographic view taken along the lines 4—4 of FIG. 3 in the direction indicated by the arrows.

FIG. 5 is an isometric illustration of an accessory structure utilized by the instant invention.

FIG. 6 is an isometric illustration of an accessory structure utilized by the instant invention in structural association therewith.

FIG. 7 is an orthographic side view of a further modified tool of he instant invention.

FIG. 8 is an orthographic view taken along the lines 8—8 of FIG. 7 in the direction indicated by the arrows.

DESCRIPTION OF THE PREFERRED EMBODIMENT

Figure 1:
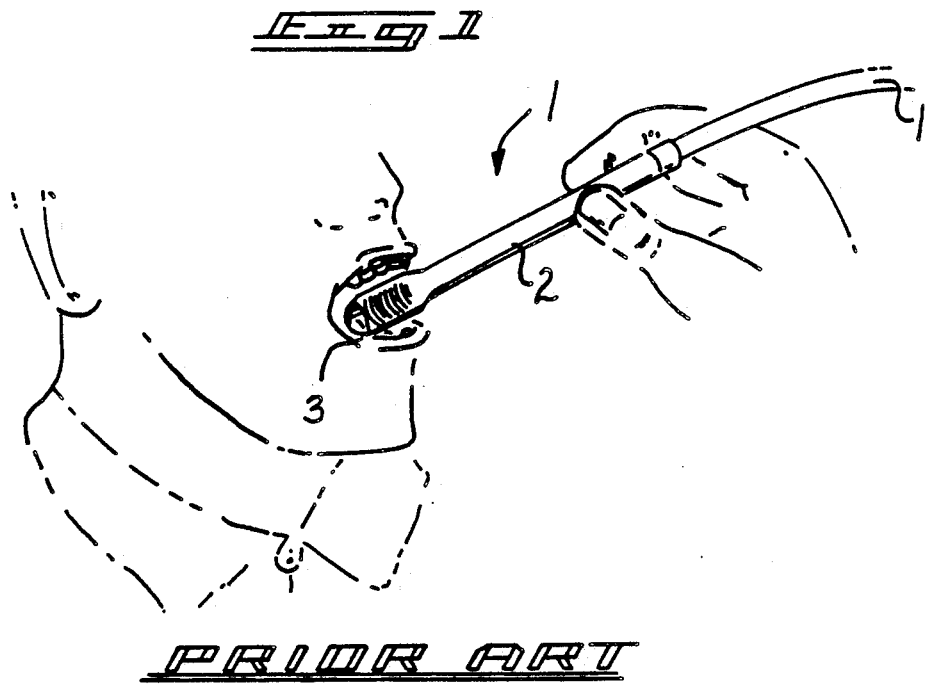
FIG. 1 is an isometric illustration of a prior art tool.

With reference now to the drawings, and in particular to FIGS. 1 to 8 thereof, a new and improved surgical suction tool embodying the principles and concepts of the present invention and generally designated by the reference numerals 10, 11 and 12 will be described.

More specifically, the surgical suction tool defines an improvement over the prior art tools, as illustrated in FIG. 1, wherein the prior art tool 1 utilizes a main rigid body in association with a vacuum tube 1 defining a forward opening 3 for positioning interiorly within an individual mouth cavity to direct fluid and debris therein interiorly of the tool and its removal from the mouth cavity.

Figure 2:
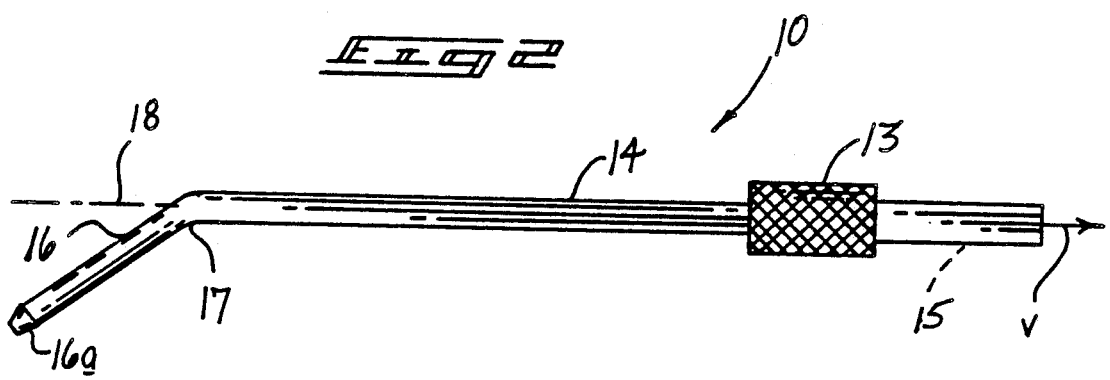
FIG. 2 is an orthographic side view of the tool of the instant invention.

FIG. 2 illustrates the instant invention defined by a knurled, spherical handle 13 of enlarged proportions relative to a main cylindrical body conduit 14 formed with a central bore 15 directed through the main cylindrical body and through a forward leg 16 terminating in a tapered forward end 16a in fluid communication with the main cylindrical body and joined therewith at a junction 17, with the central bore 15 directed through the main cylindrical body and the forward leg. The main cylindrical body includes a main cylindrical body axis 18 wherein the forward terminal end of the forward leg is spaced approximately 0.75 inches below the axis 18 and forwardly of the junction 17 approximately one inch. The tool is substantially 6.15 inches in length overall, wherein the main body 14 and leg 16 are formed by an exterior diameter of 0.1875 inches with the central bore 15 defined by a diameter of 1.25 inches, wherein the main body 14 is of enlarged diameter remote from the forward leg on the opposite side of the handle 13 of 0.250 inches to ensure its rigidity in association with a vacuum source. The tapered forward end extends coaxially of the leg 10 0.250 inches. The handle 13 is of an optimum diameter of 0.4375 inches with the main body 14 from the forward end of the handle 13 to the junction 17 a distance of 3.250 inches. The unique dimensional configuration of the aforenoted tool 10 provides a configuration convenient for universal application to individuals.

FIG. 3 is illustrative of a modified suction tool 11 defined by a modified main body 19 and defined by a lower vacuum bore 20 parallel to and aligned with an upper bore 21. The upper bore 21 contains a coextensive fiber optic cable 22 of a complementary external configuration to that defined by the upper bore 21 contained within the main body 19 which includes a first straight body portion 25 and a downwardly extending forward leg 26 terminating in a tapered forward end 26a. It should be noted that the upper and lower bores 21 and 20 respectively are coextensive with the straight body portion 25 and the forward leg 26. The externally knurled cylindrical handle 13 is as in the embodiment of FIG. 2 of an external diameter substantially greater than that and extending beyond the modified main body 19, with a fiber optic cable 22 extending rearwardly of the handle 13, as well as a vacuum connection leg 25a. A fiber optic light source connection 24 associates the fiber optic cable 22 with an illumination source (not shown) of conventional configuration to direct the light through the fiber optic cable 22 and to thereby direct the illumination thusly provided through the forward end of the forward leg 26 from illumination interiorly of an individual body cavity wherein the tool is directed.

FIG. 5 is illustrative of a plurality of relatively soft grommets 27 defined by a central aperture of an internal diameter substantially equal to that of an external diameter defined by the forward leg 16 of the tool. The grommets 27 are positioned on the forward leg of the tool in a spaced relationship to enable positioning within an individual mouth and enhance positioning of the tool within the mouth, such as by creating an abutment for the teeth or the like of the individual to properly position the tool in use.

FIGS. 7 and 8 are illustrative of a further modified suction tool 12 including a main body 28 that includes a central bore 28a that directs a vacuum source "V" therethrough from the main body 28 and through the forward leg 29 through the tapered forward end 29a. A valve 30 is positioned in a line with the main body 28 forwardly of the associated knurled handle 13. The valve 30 includes a housing 31 that includes a central chamber with a reciprocatable blade 32 positioned within the chamber and mounted to selectively impede vacuum flow through the central bore 28. The reciprocatable blade 32 includes a blade boss 33 extending upwardly through the housing 31 with an enlarged head member 34 orthogonally and integrally mounted to an upper end of the blade boss 33 with a captured coiled spring 35 secured between an upper surface of the valve 30 and a bottom surface of the enlarged head member 34 to thereby enable an individual in use of the instrument to selectively alter vacuum flow through the central bore 28a by manually depressing the head member 34.

As to the manner of usage and operation of the instant invention, the same should be apparent from the above disclosure, and accordingly no further discussion relative to the manner of usage and operation of the instant invention shall be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A surgical suction tool comprising, a main body defined by a first cylindrical tube member including a first bore, wherein the first bore is defined by a first axis, and a second cylindrical tube means including a second bore, wherein the second bore is defined by a second axis, the first bore and the second bore in angular aligned communication with one another, wherein the first axis is oriented at an obtuse angle relative to the second axis, and the first cylindrical tube terminating in a tapered forward end, the first tube and the second tube defined by as predetermined diameter, and a cylindrical knurled handle member integrally surroundingly mounted and coaxially aligned about a rear end portion of the second cylindrical tube, wherein the knurled handle member is defined by a handle diameter greater than said predetermined diameter, and a further tube in communication with said first bore directed through said handle, wherein the further tube extends rearwardly of said handle in communication with a vacuum source, and including an upper bore defined by an upper bore axis, the upper bore and upper bore axis are aligned parallel to the first tube and the second tube and spaced therefrom, the upper bore further including a fiber optic cable directed through the upper bore and defined by an external configuration complementary to that defined by an internal configuration of the upper bore, and wherein the fiber optic cable is coextensive with the first tube and the second tube and extends through the handle and rearwardly thereof, and including a fiber optic connection means for securement of the fiber optic cable to an illumination source.

2. A surgical suction tool as set forth in claim 1 further including a valve member mounted forwardly of said handle, and the valve member includes a housing in surrounding relationship to said first tube, the housing including a blade member reciprocatably mounted within said housing selectively overlying said first bore, the blade member including a blade boss directed upwardly through said housing and secured to said blade member, and said boss further including a head member orthogonally and integrally mounted to an upper end of said boss, and a coil spring captured between said head member and said housing to normally bias said blade member upwardly in said housing to permit vacuum communication between said further tube and said first cylindrical tube member and said second cylindrical tube member.

3. A surgical suction tool as set forth in claim 2 further including a first and second soft grommet selectively securable onto said second tube member in a spaced relationship thereon to provide an abutment for positioning said second tube member within a body cavity.

4. A surgical suction tool as set forth in claim 1 wherein said predetermined diameter is equal to 0.1875 inches, and said handle diameter is equal to 0.4375 inches, and said handle is defined by a handle length equal to 0.75 inches, and said first cylindrical tube member and said second cylindrical tube member are defined by a main body length equal to 4.25 inches, and said first bore and said second bore are substantially equal to 0.125 inches.

* * * * *